(12) United States Patent
Chamney et al.

(10) Patent No.: US 8,340,754 B2
(45) Date of Patent: Dec. 25, 2012

(54) METHOD AND A DEVICE FOR DETERMINING THE HYDRATION AND/OR NUTRITION STATUS OF A PATIENT

(75) Inventors: Paul Chamney, Herts (GB); Peter Wabel, Darmstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 466 days.

(21) Appl. No.: 11/630,965

(22) PCT Filed: Dec. 21, 2004

(86) PCT No.: PCT/EP2004/014544
§ 371 (c)(1),
(2), (4) Date: Dec. 28, 2006

(87) PCT Pub. No.: WO2006/002685
PCT Pub. Date: Jan. 12, 2006

(65) Prior Publication Data
US 2008/0071147 A1    Mar. 20, 2008

(30) Foreign Application Priority Data
Jun. 29, 2004  (WO) ................ PCT/EP2004/007023

(51) Int. Cl.
*A61B 5/05* (2006.01)
(52) U.S. Cl. ........................................ 600/547; 600/300
(58) Field of Classification Search .............. 600/300, 600/547
See application file for complete search history.

(56) References Cited

U.S. PATENT DOCUMENTS

| 4,895,163 | A | 1/1990 | Libke et al. |
|---|---|---|---|
| 5,449,000 | A * | 9/1995 | Libke et al. ................ 600/547 |
| 6,615,077 | B1 | 9/2003 | Zhu et al. |
| 6,643,542 | B1 * | 11/2003 | Kawanishi ................ 600/547 |
| 2004/0077968 | A1 * | 4/2004 | Simond et al. ............. 600/547 |
| 2005/0004491 | A1 * | 1/2005 | Shiokawa et al. ........... 600/547 |

FOREIGN PATENT DOCUMENTS
EP  0 343 928 A2  11/1989
(Continued)

OTHER PUBLICATIONS

Wang et al. "Disparate Hydration of Adipose and Lean Tissue Require a New Model for Body Water Distribution in Man" Journal of Nutrition 1797. pp. 1687-1693.*
Wang et al. "Disparate Hydration of Adipose and Lean Tissue Require a New Model for Body Water Distribution in Man" Jun. 1975 as submitted by applicant.*

(Continued)

*Primary Examiner* — Max Hindenburg
*Assistant Examiner* — Renee Danega
(74) *Attorney, Agent, or Firm* — Jacobson Holman PLLC (57) ABSTRACT

The invention relates to the field of monitoring the hydration and/or nutrition status of a patient. According to the invention a method is provided to determine at least one of a mal-hydration component, an adipose tissue component and a lean tissue component of a patient comprising the steps of determining chemical or physical properties of the patient and deriving the at least one component on the basis of the determined chemical or physical properties of the patient and previously determined values of a mass or volume fraction of water in lean tissue and a mass or volume fraction of water in adipose tissue. The invention also relates to a device for carrying out the method according to the invention and to a computer program product to be used on such a device.

15 Claims, 3 Drawing Sheets

FOREIGN PATENT DOCUMENTS

| | | |
|---|---|---|
| EP | 0 865 763 A2 | 9/1998 |
| EP | 1 205 144 A1 | 5/2002 |
| WO | WO 92/19153 | 11/1992 |
| WO | WO 02/36004 A1 | 5/2002 |
| WO | WO 03/030735 A1 | 4/2003 |
| WO | WO 03/053239 * | 7/2003 |
| WO | WO 03/053239 A1 | 7/2003 |
| WO | WO 2006/002656 A1 | 1/2006 |

OTHER PUBLICATIONS

Kvist et al. "Adipose tissue volume determination in males by computed tomography and 40k" Int. Journal of Obesity 1988; abstract.*

Ellis, K.J., "Human Body Composition: In Vivo Methods," Physiological Reviews, vol. 80, No. 2, pp. 649-680, Apr. 2000.

* cited by examiner

| parameter | value | description |
|---|---|---|
| $\Lambda_{LT}$ | 0.742 | fraction of water mass per unit mass of lean tissue |
| $\Lambda_{ECW,LT}$ | 0.280 | fraction of extracellular water mass per unit mass of lean tissue |
| $\Lambda_{ICW,LT}$ | 0.462 | fraction of intracellular water mass per unit mass of lean tissue |
| $\Lambda_{AT}$ | 0.194 | fraction of water mass per unit mass of adipose tissue |
| $\Lambda_{ECW,AT}$ | 0.135 | fraction of extracellular water mass per unit mass of adipose tissue |
| $\Lambda_{ICW,AT}$ | 0.059 | fraction of intracellular water mass per unit mass of adipose tissue |

METHOD AND A DEVICE FOR DETERMINING THE HYDRATION AND/OR NUTRITION STATUS OF A PATIENT

This is a nationalization of PCT/EP2004/014544 filed 21 Dec. 2004 and published in English.

The invention relates to the field of monitoring the hydration and/or nutrition status of a patient.

The kidneys carry out several functions for maintaining the health of a human body. First, they control the fluid balance by separating any excess fluid from the patient blood volume. Second, they serve to purify the blood from any waste substances like urea or creatinine. Last not least they also control the levels of certain substances in the blood like electrolytes in order to ensure a healthy and necessary concentration level.

In case of renal failure ingested fluid accumulates in body tissues and the vascular system causing increased stress on the circulatory system. This surplus fluid has to be removed during a dialysis treatment by ultrafiltration of the blood. If insufficient fluid is removed the long term consequences can be severe, leading to high blood pressure and cardiac failure. Cardiac failure itself is many times more likely to occur in dialysis patients and it is thought that states of fluid overload are one of the major contributing factors. Removal of too much fluid is also dangerous since the dialysis patient becomes dehydrated and this invariably leads to hypotension.

The dry weight (for the sake of simplicity the words "weight" and "mass" shall be used synonymously throughout this patent application document—which also is usual practise in the medical field) defines the weight of a patient that would be achieved if the kidneys were working normally. In other words this represents the optimal target weight (or fluid status) which should be achieved in order to minimise cardiovascular risk. Dry weight has always been an elusive problem in routine clinical practise due to lack of quantitative methods for its assessment. Currently the dry weight problem is approached using indirect indicators like e.g. blood pressure, echocardiographic investigations and subjective information such as X-rays. Furthermore it has been particularly difficult to define a set of conditions which are universally accepted as the dry weight standard.

A promising method to derive the fluid status of a patient involves the use of bioimpedance measurements. A small alternating current is applied to two or more electrodes which are attached to a patient and the corresponding electric potential difference is measured. The various fluid compartments of a human body contribute differently to the measured signals. The use of multiple frequencies allows the water in the intracellular volume (ICV) and the extracellular volume (ECV) to be determined. An example of such a device is described in the international patent application WO 92/19153. However, this document discloses no method regarding how the dry weight of the particular patient can be derived.

U.S. Pat. No. 5,449,000 describes a bioimpedance system also using multiple frequencies to determine water mass in the ECV and ICV. Furthermore certain population dependent data are taken for using and choosing so-called population prediction formulas. The body composition is then analysed by using these formulas and with the help of segmental bioimpedance signals.

The international patent application WO 02/36004 A1 describes a method and a device for deriving the dry weight of a patient with renal failure using a bioimpedance device by extrapolating an excess water volume in the extracellular volume to a condition where there would be no renal failure. By a similar procedure a mass correction term accounting for deviations within healthy human beings and being attributed to certain tissues can be derived.

The international patent application WO 03/053239 A1 discloses a compartmental model which addresses the variation in healthy human beings in certain body compartments in order to better separate a mal-hydration volume and other tissue components in particular with the aid of bioimpedance measurements. With such a device information on the nutrition status of a patient can also be obtained.

U.S. Pat. No. 6,615,077 describes an approach for monitoring a dialysis treatment by a bioimpedance device in order to correlate the signals with the progress of the treatment.

In view of the prior art there is a need for a simple method that requires only very few fundamental parameters and that nonetheless provides reliable results on the hydration, nutrition and training status of a patient at the same time. It is an object of this invention to provide such a method.

The problem of the invention is solved by a method according to claim 1, i.e. by a method to determine at least one of a mal-hydration component, an adipose tissue component and a lean tissue component of a patient comprising the steps of determining chemical or physical properties of the patient and deriving the at least one component on the basis of the determined chemical or physical properties of the patient and previously determined values of a mass or volume fraction of water in lean tissue and a mass or volume fraction of water in adipose tissue.

The invention is based on the observation that a model dividing the body of a patient into a lean tissue compartment, an adipose tissue compartment and a mal-hydration compartment is already adaquate to minimise the number of parameters involved and to still provide reliable results. The inventors further recognised that it is sufficient to establish values for a water volume or mass fraction for the lean tissue on one hand and for the adipose tissue on the other hand. To apply the model these fractions can be taken as fixed values independent of the patient the method is applied to. According to the concept of the invention it is, apart from the mal-hydration water compartment, mainly the individual mixture of these two types of tissues that contributes to the differential water distribution within the patient so that it is sufficient to explicitly consider these two types of tissues for this aspect.

In the framework of the invention adipose tissue is considered to consist of fat cells or adipocytes suspended in extracellular fluid. The adipocytes themselves consist predominantly of lipids or fat and a small quantity of intracellular fluid. Adipose tissue should therefore not be confused with fat even though they are related. Fat is simply the pure lipid whilst adipose tissue is a mixture of fat and water. The adipocytes bind a proportion of extracellular fluid which makes up the total adipose tissue mass. This extracellular fluid is therefore not free fluid and must be taken into account when calculating a patient's excess fluid.

In the prior art two-compartment models have been known that divide the human body into a fat-free mass and a fat mass compartment (e.g.: K. J. Ellis, "Human Body Composition: In Vivo Methods", Physiological Reviews 80, 649 (2000)). In such a model the fat mass compartment only consists of fat or lipids whereas the remainder of the body, including the water, is lumped together in the fat-free mass compartment. This is different to the present invention that distinguishes between adipose tissue—including a non-vanishing water component—on one hand and lean tissue on the other hand. Though the lean tissue compartment is—apart from the mal-hydration compartment—again defined as the "remainder" of the body mass, the two tissues are further distinguished by their different water fractions.

It is also an object of the invention to provide a device for a non-invasive, accurate and easy to use body compartment assessment. The invention therefore also concerns a device according to claim 9 for carrying out the method according to the invention, i.e. a device comprising a measurement and/or input unit configured to provide values for chemical or physical properties of the patient to be determined, an evaluation unit configured to derive at least one component of a mal-hydration component, an adipose tissue component and a lean tissue component on the basis of the determined chemical or physical properties of the patient and previously determined values of a mass or volume fraction of water in lean tissue and a mass or volume fraction of water in adipose tissue, and a communication link between the measurement and/or input unit and the evaluation unit.

In a preferred embodiment the evaluation unit is also configured to control the measurement and/or input unit for determining at least one of the chemical or physical properties of the patient.

In a further preferred embodiment the evaluation unit is a microprocessor unit which in turn comprises a microprocessor program storage unit, wherein in the microprocessor program storage unit a program for deriving the at least one component on the basis of the determined chemical or physical properties of the patient and previously determined values of a mass or volume fraction of water in lean tissue and a mass or volume fraction of water in adipose tissue is stored.

A computer program product which comprises a storage medium on which a computer program is stored which is to be stored in a device according to the invention for carrying out the method according to the invention where the evaluation unit comprises a microprocessor storage unit, is also constituting a part of the invention.

Various further embodiments of the invention are subject of the subclaims of the independent claims.

For an improved understanding of the invention, non-restrictive examples will be described with reference to the appended drawings in which.

Figure 1A:
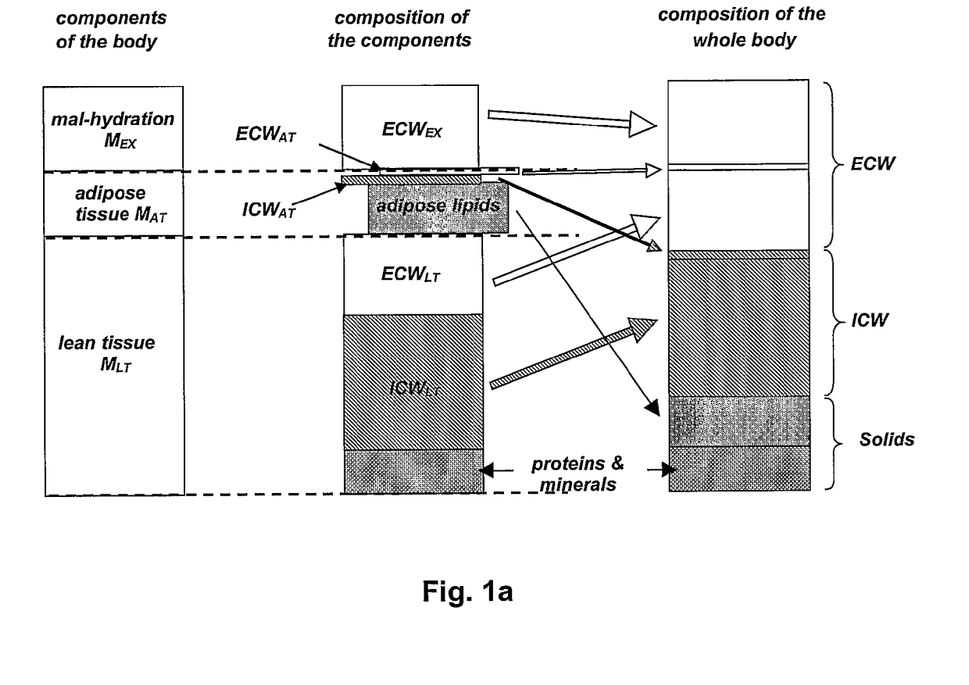
FIG. 1a shows a schematic illustration of the three components of the body of a patient representing the mal-hydration mass $M_{EX}$, the lean tissue mass $M_{LT}$ and the adipose tissue mass $M_{AT}$.

As illustrated in FIG. 1a the body of a patient can be divided into three components: an excess fluid or mal-hydration component with mass $M_{EX}$, a lean tissue component with mass $M_{LT}$ and an adipose tissue component with mass $M_{AT}$. For all three components the extracellular water (ECW) and intracellular water (ICW) together with other contributions (minerals, proteins, lipids etc.) are also shown in FIG. 1a. The excess fluid $M_{EX}$ which mainly accumulates in the ECV space is an indicator of the mal-hydration status of a patient. In a healthy subject $M_{EX}$ would be vanishing. $M_{EX}$ may also have a negative value indicating a hydration status where the patient is over hydrated.

The lean and the adipose tissue are distinguished in the framework of this application by their water contents. The lean tissue mass $M_{LT}$ comprises bones, organs (including blood) and muscles, but no lipids. More sophisticated models could be considered to include the influence of bone or other tissues, but for the present purpose such refinements are neglected. Adipose tissue mass $M_{AT}$, on the other hand, is assumed to be largely comprised of lipids and water in the form of fat cells or adipocytes.

According to the concept of the invention it is necessary to distinguish between the mass fraction $\Lambda_{LT}$ of water in lean tissue as a first tissue and the corresponding mass fraction $\Lambda_{AT}$ of water in adipose tissue as a second tissue:

$$\Lambda_{LT} \equiv \frac{D \cdot (ECW_{LT} + ICW_{LT})}{M_{LT}}, \quad (1)$$

$$\Lambda_{AT} \equiv \frac{D \cdot (ECW_{AT} + ICW_{AT})}{M_{AT}}, \quad (2)$$

wherein D is the density of water (D=0.99823 kg/liter at 36° C.; for the present purpose a single density value is considered to be sufficient, however small variations due to solutes in the different water compartments may be introduced), $ECW_{LT}$ and $ICW_{LT}$ are the volumes of extracellular and intracellular water in the lean tissue, the latter having the total mass $M_{LT}$, and $ECW_{AT}$ and $ICW_{AT}$ are the volumes of extracellular and intracellular water in the adipose tissue, the latter having the total mass $M_{AT}$. Eqs. (1) and (2) may of course also be written in terms of fractions per tissue volume, as volume per mass or as mass per volume without leaving the concept of the invention. It is only important that the water contribution to the lean tissue on one hand and to the adipose tissue on the other hand is considered differently.

The fractions $\Lambda_{LT}$ and $\Lambda_{AT}$ each have a contribution $\Lambda_{ECW}$ from the extracellular water and a contribution $\Lambda_{ICW}$ from the intracellular water:

$$\Lambda_{ECW,LT} \equiv \frac{D \cdot ECW_{LT}}{M_{LT}}, \quad (3)$$

$$\Lambda_{ICW,LT} \equiv \frac{D \cdot ICW_{LT}}{M_{LT}}, \quad (4)$$

$$\Lambda_{ECW,AT} \equiv \frac{D \cdot ECW_{AT}}{M_{AT}}, \quad (5)$$

$$\Lambda_{ICW,AT} \equiv \frac{D \cdot ICW_{AT}}{M_{AT}}. \quad (6)$$

According to the concept of the present invention it is sufficient to previously determine at least values for the mass fractions $\Lambda_{LT}$ and $\Lambda_{AT}$. In more refined embodiments of the invention the mass fractions as defined by some or all the Eqs. (3) to (6) are used. To determine such values various experimental methods may be employed. Once these values are established, as will be shown below, a set of rather simple equations may be used for routine application that can also be employed together with less sophisticated experimental methods but still lead to accurate and reliable results for the masses of the three body components $M_{EX}$, $M_{LT}$ and $M_{AT}$.

Using dual x-ray absorptiometry (DXA) or dilution experiments as reference data it is possible to derive the mass fractions of extracellular and intracellular water independently for the lean tissue and the adipose tissue mass components. A good review of such and other methods is given in the aforementioned article from K. J. Ellis.

Figure 1B:
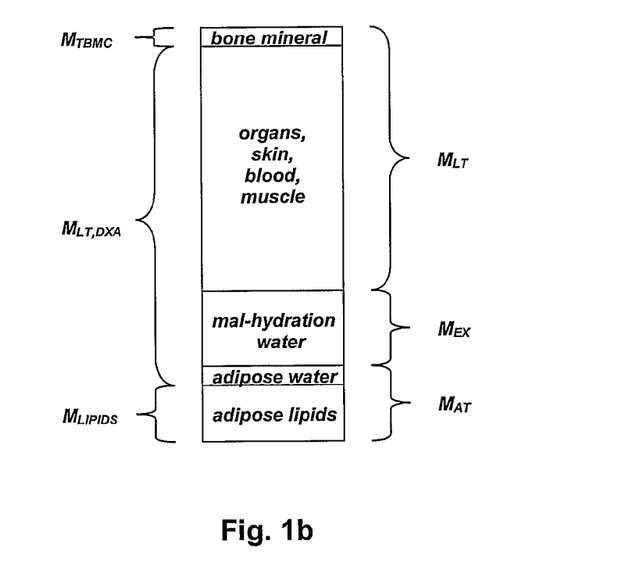
FIG. 1b shows a schematic illustration of the three components of a body of a patient according to FIG. 1a (right hand side) in relation to the mass components as derived by dual x-ray absorptiometry (DXA) (left hand side)

In DXA the attenuation of two x-ray photons having different photon energies is compared. As a result it is possible to distinguish between fat mass $M_{LIPID}$, lean tissue mass $M_{LT,DXA}$ according to DXA and the total bone mineral content mass $M_{TBMC}$ of a patient. The relation of these mass components to the components as used by the invention is shown in FIG. 1b. It is important to note that the fat mass $M_{LIPID}$ does only represent the adipose lipids of the adipose tissue, but not the adipose water. Furthermore, the lean tissue mass $M_{LT}$ comprises parts of the lean tissue mass $M_{LT,DXA}$ according to DXA and the total bone mineral content mass $M_{TBMC}$. The lean tissue mass $M_{LT,DXA}$ according to DXA, on the other hand, also comprises the mal-hydration mass $M_{EX}$ and the adipose water mass.

With the help of dilution experiments as a further reference method certain compartments of a body can be probed by selecting appropriate tracer substances that dilute just in the chosen compartment. Typical examples are the ECW, ICW or the total body water (TBW) volumes.

Figure 2:
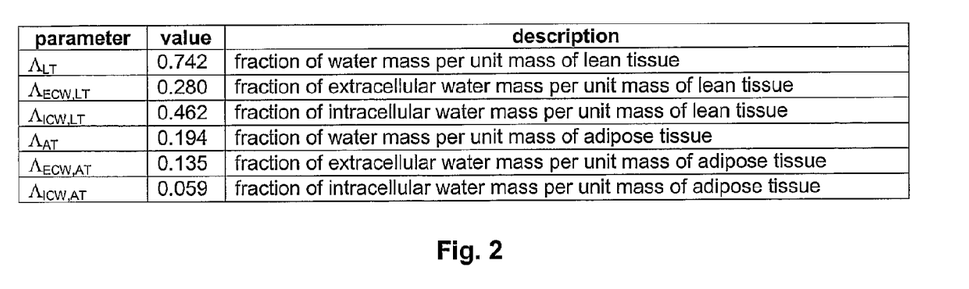
FIG. 2 shows a compilation of example values for the various parameters required in the example embodiments of the invention for the calculation of the body mass components, FIG. 3 schematically shows an embodiment of a device for the assessment of the body composition of a patient according to the present invention.

Taking the reference data from such experiments the mass fractions of Eqs. (1) to (6) can be derived by optimisation and also by analytical methods in an effort to map the observed data as closely as possible for as many individuals as possible. An example result of such a procedure is compiled in FIG. 2.

Once at least one of the water mass fractions $\Lambda_{LT}$, $\Lambda_{ECW,LT}$ or $\Lambda_{ICW,LT}$ of the lean tissue mass component and at least one of the water mass fractions $\Lambda_{AT}$, $\Lambda_{ECW,AT}$ or $\Lambda_{ICW,AT}$ of the adipose tissue mass component have been previously determined it is now possible to derive vice versa at least one of the masses of the mal-hydration mass $M_{EX}$, the lean tissue mass $M_{LT}$ and the adipose tissue mass $M_{AT}$ from routine experimental measurement data of chemical or physical properties of the patient without having to use all the experimental methods that were applied to obtain the reference data. Depending on the kind of chemical or physical properties that are to be determined by the routine measurements, various modes of the invention are possible. Before an exemplary device according to the invention will be explained in detail five examples for such methods according to the invention are described:

EXAMPLE 1

Chemical or physical properties of the patient to be determined:
ECW: volume of the total extracellular water of the patient,
ICW: volume of the total intracellular water of the patient,
M: whole body mass of the patient.

Each of these properties can be split into contributions from the three components:

$$ECW = ECW_{EX} + ECW_{LT} + ECW_{AT} \quad (7),$$

$$ICW = ICW_{LT} + ICW_{AT} \quad (8),$$

$$M = M_{LT} + M_{AT} + M_{EX} \quad (9).$$

Using Eqs. (3) to (6), Eqs. (7) to (9) can be solved for the masses of all three components:

$$M_{EX} = \frac{D \cdot ECW - M \cdot (\Lambda_{ECW,AT} + k_1 \Lambda_{ICW,AT}) + k_1 D \cdot ICW}{(1 - \Lambda_{ECW,AT} - k_1 \Lambda_{ICW,AT})} \quad (10)$$

wherein $$k_1 = \frac{\Lambda_{ECW,AT} - \Lambda_{ECW,LT}}{\Lambda_{ICW,LT} - \Lambda_{ICW,AT}}, \quad (11)$$

$$M_{LT} = \frac{D \cdot ICW - (M - M_{EX}) \cdot \Lambda_{ICW,AT}}{(\Lambda_{ICW,LT} - \Lambda_{ICW,AT})} \quad (12)$$

and $$M_{AT} = M - M_{LT} - M_{EX}. \quad (13)$$

EXAMPLE 2

Chemical or physical properties of the patient to be determined:
TBW: volume of the total body water of the patient
$M_{TBMC}$: mass of total bone mineral content of the patient
M: whole body mass of the patient.

The total body water TBW can be split into three parts originating from the three components:

$$TBW = \frac{1}{D}(\Lambda_{LT} \cdot M_{LT} + \Lambda_{AT} \cdot M_{AT} + M_{EX}). \quad (14)$$

The lean tissue mass $M_{LT}$ is split in this example into its water fraction and a rest fraction $M_{Min+Pro}$ mainly attributing for minerals and proteins:

$$M_{LT} = \Lambda_{LT} M_{LT} + M_{Min+Pro} \quad (15).$$

Taking $k_{TBMC}$ to be the share of the total bone mineral content mass $M_{TBMC}$ of $M_{Min+Pro}$ one has:

$$M_{TBMC} = k_{TBMC} \cdot M_{Min+Pro} \quad (16)$$

wherein a typical value of $k_{TBMC}$ is 0.2074. Together with the mass balance Eq. (9) the set of Eqs. (14) to (16) can be solved for the three component masses:

$$M_{EX} = \frac{D \cdot TBW - \frac{M_{TBMC}}{k_{TBMC}(1 - \Lambda_{AT})}(\Lambda_{LT} - \Lambda_{AT}) - \Lambda_{AT} \cdot M}{(1 - \Lambda_{AT})}, \quad (17)$$

$$M_{LT} = \frac{M_{TBMC}}{k_{TBMC}(1 - \Lambda_{LT})} \quad (18)$$

and $M_{AT}$ is obtained by using Eq. (13).

EXAMPLE 3

Chemical or physical properties of the patient to be determined:
TBW: volume of the total body water of the patient
$M_{LIPID}$: lipid mass of the patient
M: whole body mass of the patient.

The mass of mal-hydration water can be expressed as $$M_{EX} = D(TBW - TW_{LT} - TW_{AT}) \quad (19),$$

wherein $TW_{LT}$ is the sum of the extra- and intracellular water volumes in the lean tissue and $TW_{AT}$ is the sum of the extraand intracellular water volumes in the adipose tissue. The lipid mass $M_{LIPID}$ of the patient is the mass $M_{AT}$ of the adipose tissue without the water mass in the adipose tissue:

$$M_{LIPID} = M_{AT} - D \cdot TW_{AT} = M_{AT}(1 - \Lambda_{AT}) \qquad (20).$$

Inserting Eqs. (13) and (20) in Eq. (19) by making use of Eqs. (1) and (2) and solving for the mal-hydration water mass $M_{EX}$ one obtains:

$$M_{EX} = \frac{D \cdot TBW - \Lambda_{LT}M + \frac{M_{LIPID}}{1 - \Lambda_{AT}}(\Lambda_{LT} - \Lambda_{AT})}{(1 - \Lambda_{LT})} \qquad (21)$$

$M_{AT}$ may be calculated by solving Eq. (20) and $M_{LT}$ by solving Eq. (9):

$$M_{AT} = \frac{M_{LIPID}}{(1 - \Lambda_{AT})} \text{ and} \qquad (22)$$

$$M_{LT} = M - M_{AT} - M_{EX}. \qquad (23)$$

EXAMPLE 4

Chemical or physical properties of the patient to be determined:
ECW: volume of the total extracellular water of the patient
$M_{LIPID}$: lipid mass of the patient
M: whole body mass of the patient.
The mass of mal-hydration water can be expressed as $$M_{EX} = D(ECW - ECW_{LT} - ECW_{AT}) \qquad (24),$$

wherein the parameters are as defined in Example 1. Inserting Eqs. (13) and (22) in Eq. (24) by making use of Eqs. (2), (3) and (5) and solving for the mal-hydration water mass $M_{EX}$ one obtains:

$$M_{EX} = \frac{D \cdot ECW - \Lambda_{ECW,LT}M + \frac{M_{LIPID}}{1 - \Lambda_{AT}}(\Lambda_{ECW,LT} - \Lambda_{ECW,AT})}{(1 - \Lambda_{ECW,LT})} \qquad (25)$$

$M_{AT}$ and $M_{LT}$ may be derived similar as in Example 3, i.e. according to Eqs. (22) and (23).

EXAMPLE 5

Chemical or physical properties of the patient to be determined:
ECW: volume of the total extracellular water of the patient
ICV: volume of the total intracellular cells of the patient
M: whole body mass of the patient.
This example has similarities with Example 1. However, instead of the ICW the intracellular volume ICV as a whole, including the volume of matter not being water is determined. In this case it is useful to introduce further constants that are related to the water mass fractions as defined by Eqs. (3) to (6).
In analogy to the ICW the total ICV can be split into components $ICV_{AT}$ for the adipose tissue and $ICV_{LT}$ for the lean tissue. These are linked to the masses $M_{LT}$ of the lean tissue component and $M_{AT}$ of the adipose tissue component by proportionality constants $\zeta_{LT}$ and $\zeta_{AT}$ (example values as taken from the international patent application PCT/EP2004/007023 are $\zeta_{LT}$=0.620 liters/kg and $\zeta_{AT}$=0.987 liters/kg):

$$ICV = ICV_{LT} + ICV_{AT} = M_{LT} \cdot \zeta_{LT} + M_{AT} \cdot \zeta_{AT} \qquad (26).$$

Substituting $M_{AT}$ in Eq. (26) with the help of Eq. (9) and solving the resultant equation for $M_{LT}$, Eq. (27) is obtained:

$$M_{LT} = \frac{ICV - \zeta_{AT}(M - M_{EX})}{\zeta_{LT} - \zeta_{AT}}. \qquad (27)$$

Before the lean tissue mass $M_{LT}$ can be derived, the mal-hydration mass $M_{EX}$ has to be calculated. The starting point is again the observation that this component manifests itself entirely in the ECV space, i.e. the mal-hydration water volume can be derived as $ECW_{EX}$ by solving Eq. (7).

Using the following definitions for the volume of extracellular water per unit mass of lean tissue $\lambda_{ECW,LT}$, $$\lambda_{ECW,LT} \equiv \frac{ECW_{LT}}{M_{LT}} = \frac{\Lambda_{ECW,LT}}{D} \qquad (28)$$

and for the volume of extracellular water per unit mass of adipose tissue $\lambda_{ECW,AT}$, $$\lambda_{ECW,AT} \equiv \frac{ECW_{AT}}{M_{AT}} = \frac{\Lambda_{ECW,AT}}{D}, \qquad (29)$$

and further introducing the definition $$A \equiv \frac{\lambda_{ECW,LT} - \lambda_{ECW,AT}}{\zeta_{LT} - \zeta_{AT}}, \qquad (30)$$

Eq. (7) can be solved with the help of Eqs. (9) and (27):

$$ECW_{EX} = \frac{ECW - A \cdot ICV + (A \cdot \zeta_{AT} - \lambda_{ECW,AT}) \cdot M}{(1 + (A \cdot \zeta_{AT} - \lambda_{ECW,AT})D_{ECW})} \qquad (31)$$

wherein $D_{ECW}$ is the density of the extracellular water (=0.99823 kg/liter). Once the mal-hydration volume $ECW_{EX}$ has been determined (and thus the mal-hydration mass $M_{EX}$), the lean tissue mass $M_{LT}$ can be calculated from Eq. (27) and the adipose tissue mass $M_{AT}$ by Eq. (13).

As can be seen from all five examples, the chemical or physical properties that have to be determined of the patient may vary from one example to another. It is yet in all examples possible to determine at least one of a mal-hydration component, an adipose tissue component and a lean tissue component of the patient on the basis of the determined chemical or physical properties and previously determined values of a mass or volume fraction of water in lean tissue and a mass or volume fraction of water in adipose tissue. The general concept of the present invention is therefore not limited to specific methods where specific properties of a patient have to be determined. The key element of the invention to derive the at least one body component is to make appropriate use of the previous determined values of a mass or volume fraction of water in lean tissue and a mass or volume fraction of water in adipose tissue. The same applies not just to the method but also to any device according to the invention.

Figure 3:
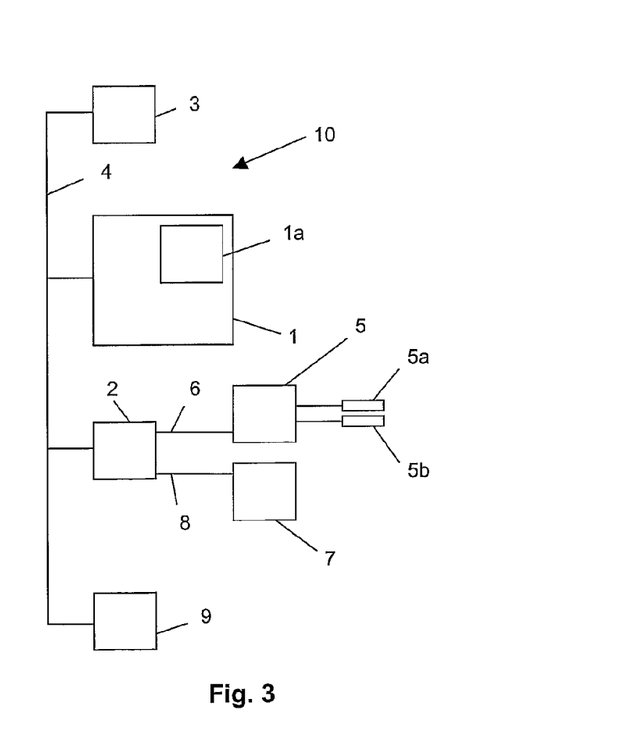

The method according to Example 1 is now used to describe an embodiment of a device according to the invention in detail (FIG. 3). The device 10 comprises an evaluation unit that consists of a microprocessor unit 1 which in turn comprises a microprocessor program storage unit 1a. By means of a communication link 4 the microprocessor unit 1 is connected to an interface unit 2 and a computer storage unit 3. A program for determining the masses $M_{EX}$, $M_{LT}$ and/or $M_{AT}$ of a patient is stored in the microprocessor program storage unit 1a. This program may have been transferred beforehand to the microprocessor program storage unit 1a from a computer program product like a floppy disk, a CD-ROM, a DVD, a memory stick, a server or any other suitable storage medium on which the program was stored. In this case the device 10 comprises the necessary interface circuitry (not shown) whose design is—dependent of the type of computer program product—obvious to a person skilled in the art.

The microprocessor program controls the device to determine patient impedance values for two or more frequencies. For the corresponding measurement the device 10 comprises a bioimpedance measurement means 5 which is connected to the interface unit 2 by a communication link 6. The bioimpedance measurement means 5 can be capable of automatically compensating for influences on the impedance data like contact resistances. An example for such a bioimpedance measurement means 5 is a device from Xitron Technologies distributed under the trademark Hydra™ and also described in WO 92/19153.

Figure 4:
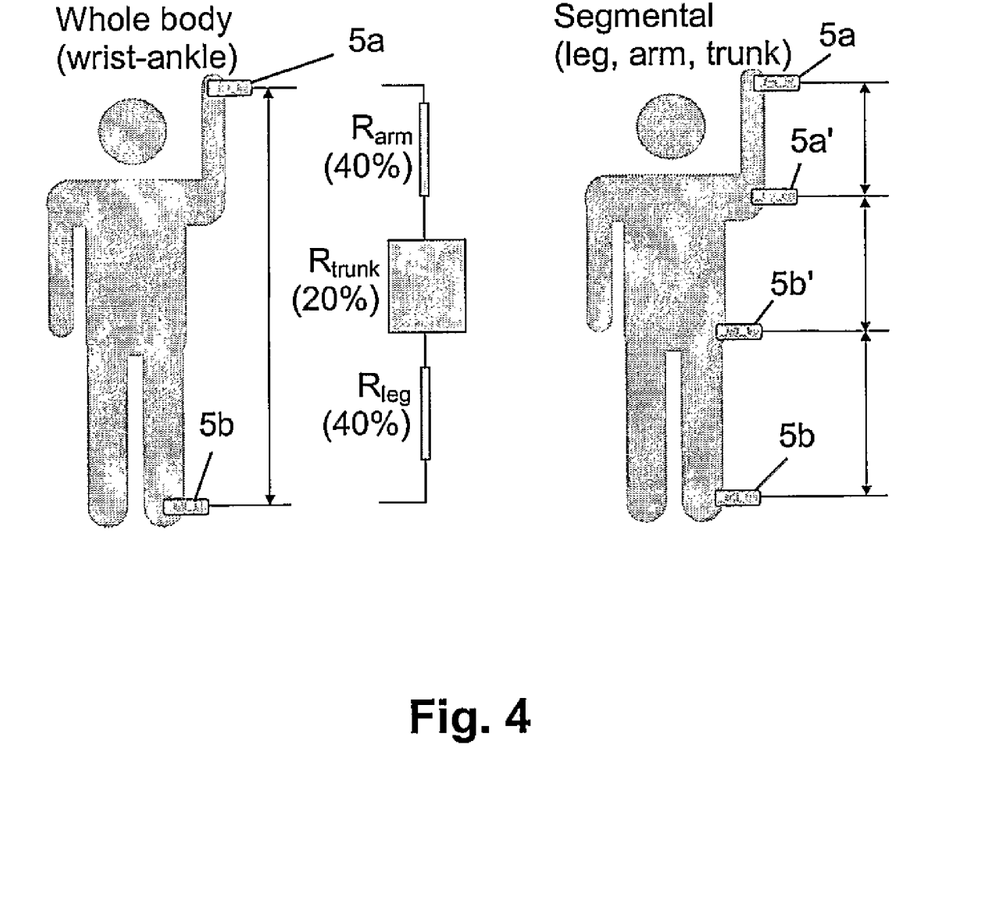
FIG. 4 shows a bioimpedance electrode arrangement for whole body bioimpedance measurements (left hand side) and a bioimpedance electrode arrangement for segmental body bioimpedance measurements (right hand side).

For the bioimpedance measurement various electrode arrangements are possible. In FIG. 3 only two electrode elements 5a and 5b are attached to the bioimpedance measurement device 5. Each of the electrode units 5a and 5b consists of a current injection electrode and a potential pick-up electrode (not shown). By applying the two electrode units 5a and 5b to the wrist and the ankle of a patient, respectively, as outlined in the left part of FIG. 4, the whole body impedance may be determined. Under this electrode configuration the body may be regarded as a combination of several homogenous cylinders, representing trunk, legs and arms. Average contributions of these components to the total impedance are also provided in FIG. 4, mainly resulting from the differing cross-sections of the cylinders.

By using additional electrodes on shoulder and hip, these cylindrical segments may be measured separately, thereby possibly increasing the accuracy of volume determinations. Such a configuration is displayed on the right hand side of FIG. 4. Additional electrode units 5a' and 5b' are attached close to the shoulder and the hip of the patient enabling a segmental approach to the body elements leg, arm and trunk.

The program stored in the microprocessor storage unit 1a initiates an impedance measurement at least two given frequencies and records the corresponding current and voltage signals, both being below critical thresholds so that the device just non-invasively probes the patient impedance without having any impact on the patient at all. The device can easily be applied by the patient him- or herself without necessarily requiring medical staff.

Returning to the embodiment shown in FIG. 3, the weight or whole body mass M of the patient can be entered into the device 10 via any input unit (not explicitly shown) connected to or being part of the interface unit 2 (e.g. a keyboard, touch screen etc.). This may be assisted by a weighing means 7 linked to the interface unit 2 by a communication link 8.

In the embodiment shown in FIG. 3 the interface unit 2 serves as an interface by which the values of the whole body mass M and any measured impedance or applied current and voltage values are directly exchanged via the communication link 4 between the computer storage unit 3, the program stored in the microprocessor program storage unit 1a, the interface 2 and the bioimpedance measurement means 5. As indicated it is also possible that any data from or to the weighing means 7 are directly transferred between the connected components via the communication links.

The program stored in the microprocessor storage unit 1a is now—with the help of stored previously established data—processing the stored data in order to determine any contributions of various body tissues components to the whole body mass M.

As outlined above the ECW is determined by exploiting the fact that the electrical impedance of body tissue changes when alternating currents of different frequencies are applied to the patient via the electrodes. At low frequencies the cell membranes behave as insulators and the applied current passes only through the ECV spaces, i.e. the ECW volume. At high frequencies the cell membranes become more conductive and thus current passes through both the ICV and ECV spaces. Measurement of the impedance over at least two frequencies, better over a range of frequencies, allows the determination of both the ECW and the ICW. In the prior art as described above such methods have been disclosed. A more refined model was developed recently by the same inventors as of the present invention in the patent application PCT/EP2004/007023 whose disclosure is hereby explicitly enclosed in the current application by reference.

Once any values for the ECW, ICW and whole body mass M as chemical or physical properties of the patient have been determined the microprocessor program applies Eqs. (10) to (13) to receive values for at least one of a mal-hydration component, a adipose tissue component and a lean tissue component, here the masses $M_{EX}$, $M_{LT}$ and $M_{AT}$ of all three components, on the basis of previously determined values of a mass or volume fraction of water in lean tissue and a mass or volume fraction of water in adipose tissue.

The results are finally completely or partially passed on to an output unit 9 which typically is a display device which displays the results to a user. Further results—independent whether as an intermediate or as an additional result—might add to the informative character of the display.

The compartmental results may be stored in the device to enable a trend analysis including previously derived results. It has also proved useful to smooth the data by deriving weighted average values from the latest and the previous data. For this purpose various algorithms are available in the art to reduce statistical scatter in the data. A useful improvement in the averaging procedure for the current result to be displayed was obtained by giving the latest measurement the highest weight and by decreasing the weight of other, previous measurements with increasing time that has passed since the measurements were taken.

The disclosed device and method according to the invention are hence able to provide for a powerful and more accurate technique for the management of the hydration status of a patient. In case the weight $M_{AT}$ of the adipose tissue component and/or the weight $M_{LT}$ of the lean tissue component are also determined the invention is yielding useful further results which allow conclusions about the nutrition and/or training status of the patient. This is not dependent on whether the patient is really mal-hydrated or not.

It is important to note that the concept of the invention is not limited to the use of a bioimpedance measurement means on one hand and on the application of Example 1 on the other hand. For applying the concept of Example 1 it is not relevant as to how the values of the properties of the patient have been determined. In particular Examples 2, 3 and 4 provide examples of such variations of the concept of the invention. Instead of bioimpedance other techniques may be applied that are suitable to reveal the separate character of the lean tissue on one hand and the adipose tissue on the other hand. As example technique to determine the lipid mass $M_{LIPID}$ or the total bone mineral content mass $M_{TBMC}$ DXA measurements are recalled. Total body water, ICW or ECW may also be derived by dilution methods.

In the simplest embodiment of a device according to the invention such a device comprises an input unit by which such chemical or physical property values may be entered into the device. As described above such a device may also comprise at least partly the measurement means to determine the chemical or physical properties of the patient. In such a case it is possible that the evaluation unit also controls the measurement unit for carrying out the measurement of the chemical or physical properties of the patient in an automated manner.

Hence management of any individual is possible, independent of any treatment modality. The invention is particularly applicable for patients which undergo end stage renal failure treatments like hemodialysis, hemofiltration, hemodiafiltration or any forms of peritoneal dialysis (all these treatment modalities are summarised throughout this patent application by the terminology "a dialysis treatment"). A characterisation of hydration status might also be highly desirable within the intensive care setting, since highly abnormal electrolyte- and fluid conditions are frequent for such patients. Furthermore, measurement in virtually any setting where nutrition or fitness parameters are required, including home, pharmacies, medical practices, dialysis units, wards, fitness centres, etc., would be practical.

The invention claimed is:

1. A method to determine a mal-hydration component, an adipose tissue component, and a lean tissue component of a patient, the method comprising the steps of:
   (a) determining chemical or physical properties of the patient; wherein the chemical or physical properties of the patient are at least one of the whole body mass, the lipid mass and the total bone mineral content mass of the patient, and
   (b) deriving the mal-hydration component, the adipose tissue component and the lean tissue component on the basis of the determined chemical or physical properties and previously determined patient-independent values of a mass or volume fraction of water in lean tissue and a mass or volume fraction of water in adipose tissue, wherein the mal-hydration component, the adipose tissue component and the lean tissue component is the mass or volume of the patient.

2. The method according to claim 1, characterised in that the chemical or physical properties of the patient further comprises the volume or mass of at least one of the total water, the extracellular water and the intracellular water of the patient.

3. The method according claim 1, characterised in that the previously determined values comprise the mass or volume fraction of the total water in lean tissue and the mass or volume fraction of the total water in adipose tissue.

4. The method according to claim 1, characterised in that the previously determined values comprise the mass or volume fraction of extracellular water in lean tissue and the mass or volume fraction of extracellular water in adipose tissue.

5. The method according claim 1, characterised in that the previously determined values comprise the mass or volume fraction of intracellular water in lean tissue and the mass or volume fraction of intracellular water in adipose tissue.

6. A device for carrying out a method to determine a mal-hydration component, an adipose tissue component, and a lean issue component of a patient, the method comprising the steps of:
   (a) determining chemical or physical properties of the patient; and
   (b) deriving the mal-hydration component, the adipose tissue component and the lean tissue component on the basis of the determined chemical or physical properties and previously determined patient-independent values of a mass or volume fraction of water in lean tissue and a mass or volume fraction of water in adipose tissue, wherein the mal-hydration component, the adipose tissue component and the lean tissue component is the mass or volume of the patient;
   the device comprising
   a measurement and/or input unit configured to provide values for the chemical or physical properties of the patient to be determined,
   an evaluation unit configured to derive the mal-hydration component, the adipose tissue component and the lean tissue component on the basis of the determined properties of the patient and previously determined patient-independent values of a mass or volume fraction of water in lean tissue and a mass or volume fraction of water in adipose tissue, wherein the mal-hydration component, the adipose tissue component and the lean tissue component is the mass or volume of the patient, and
   a communication link between the measurement and/or input unit and the evaluation unit.

7. The device according to claim 6, characterised in that the evaluation unit is also configured to control the measurement and/or input unit for determining at least one of the chemical or physical properties of the patient.

8. The device according to claim 6, characterised in that the evaluation unit is a microprocessor unit which in turn comprises a microprocessor program storage unit, wherein a program for deriving the at least one component on the basis of the determined chemical or physical properties of the patient and previously determined patient-independent values of a mass or volume fraction of water in lean tissue and a mass or volume fraction of water in adipose tissue is stored in the microprocessor program storage unit.

9. The device according to claim 8, characterised in that the program stored in the microprocessor storage unit also controls the measurement and/or input unit for determining at least one of the chemical or physical properties of the patient.

10. The device according claim 6, characterised in that the measurement unit comprises a bioimpedance measurement means to determine at least one of the chemical or physical properties of the patient.

11. The device according to claim 10, characterised in that the at least one of the chemical or physical properties of the patient comprise at least one of the extracellular water volume, the intracellular water volume or the total body water volume of the patient.

12. The device according to claim 6, characterised in that the measurement unit comprises scales to determine at least one of the chemical or physical properties of the patient.

13. The device according to claim 12, characterised in that the at least one of the chemical or physical properties is the whole body mass of the patient.

14. The device according to claim 6, characterised in that it further comprises an output unit linked to the evaluation unit for outputting any data derived by the evaluation unit.

15. A computer program product characterised in that it comprises a storage medium on which a microprocessor program to be stored in the microprocessor program storage unit of the device according to claim 8 is stored.

* * * * *